United States Patent [19]

Punto et al.

[11] Patent Number: 5,587,149
[45] Date of Patent: Dec. 24, 1996

[54] TOPICAL APPLICATION EMULSIONS

[75] Inventors: Louis Punto, Clearwater; Chim Potini, Largo; Pilar Duque; Eva Gould, both of Tampa, all of Fla.

[73] Assignee: R.P. Scherer Corporation, Troy, Mich.

[21] Appl. No.: 383,782

[22] Filed: Feb. 6, 1995

[51] Int. Cl.$^6$ ....................................................... A61K 7/42
[52] U.S. Cl. ............................ 424/59; 424/401; 424/456; 514/474; 514/844
[58] Field of Search ................................... 424/401, 456, 424/59; 514/557, 844

[56] References Cited

U.S. PATENT DOCUMENTS 5,039,513  8/1991  Chatterjee ................................. 424/47
5,082,661  1/1992  Meenik ..................................... 424/401

*Primary Examiner*—Jane Fan
*Assistant Examiner*—Evelyn Huang
*Attorney, Agent, or Firm*—Banner & Witcoff, Ltd.

[57] ABSTRACT

The present invention relates in general to products for topical application to the skin, and more particularly to improved stable emulsions for containing water soluble active ingredients, such as Vitamin C, glycolic acid, etc., which may nonetheless be packaged with gelatin capsules, and which have demonstrated improved stability.

In particular, the invention relates to a novel polyethylene glycol-in-oil emulsion that is compatible with gelatin capsules.

8 Claims, 1 Drawing Sheet

TOPICAL APPLICATION EMULSIONS

BACKGROUND OF THE INVENTION

The present invention relates in general to products for topical application to the skin, and more particularly to improved, stable emulsions for carrying active ingredients, such as for example, Vitamin C, glycolic acid, etc., the combination of which may be packaged in gelatin capsules, preferably soft gelatin capsules, as well as other packaging structures. In particular, the invention in its broad embodiments relates to a novel polyethylene glycol (PEG) in oil emulsion. These emulsions are in the preferred mode of packaging compatible with gelatin capsules.

Vitamin C, i.e., ascorbic acid, is known as being suitable for preventing or treating a variety of skin pathologies or diseases. Vitamin C is described as being protective of damage caused by UV-A and UV-B radiation. Among the diseases that can be treated or prevented with Vitamin C therapy, i.e., antioxidant therapy, are UV-B radiation-induced erythema, photoaging of the skin, skin cancer, etc.

It is known in the art that unmodified gelatin capsules are incompatible with water. Accordingly, typical emulsions (Oil-in-Water or Water-In-Oil) will degrade a capsule shell made of gelatin. The present novel methods and combination of ingredients permit the formation of cosmetically acceptable emulsions that will be tolerated by gelatin capsules. One additional advantage of these PEG-in-oil emulsions, in combination with gelatin capsules, is the capacity for use of an increased percentage of water soluble actives that can be encapsulated versus typical anhydrous bases which cannot tolerate water soluble actives. For example, ingredients such as vitamin C, which would have a low solubility in an anhydrous base, can be incorporated at higher levels using the emulsion systems of the present invention.

However, the use of PEG as the primary solubilizer for water soluble actives in gelatin capsules is not without additional problems in need of solving. In fact, from a cosmetic aesthetic perspective, the resultant emulsion carrier would in many applications be unacceptable, as PEG has a poor feel on the skin.

Thus, one difficulty overcome in developing such an emulsion system has been the modification of a predominately PEG-based product to create a better skin feel, so that it would (a) be aesthetically acceptable to the consumer, and (b) be encapsulatable in commonly used gelatin capsules.

Accordingly, one substantial advantage of the present invention is that water soluble actives can be dissolved into PEG, emulsified into an oil base with the resultant end product having a cosmetically acceptable feel, and still be compatible in ordinary gelatin capsules.

Some of the contemplated commercial uses for the present invention would be in the area of skin treatment cosmetics. Such inventive emulsions could, for example, be used for face or body products requiring certain designated water soluble actives which would be incompatible in an anhydrous base.

Other uses, advantages and objects of the improved emulsion systems of the present invention will become known to those skilled in the art upon review of the more detailed description of the present invention set forth hereinbelow.

SUMMARY OF THE INVENTION

The improved emulsions for topical application of the present invention are especially adapted for carrying a desired water soluble active ingredient which is insoluble or substantially insoluble in an anhydrous base.

In its broad parameters, the emulsions of the present invention for topical application include first and second emulsion phases, along with a dispersing agent(s) to create an emulsion therebetween.

The first emulsion phase includes polyethylene glycol (PEG) as a solvent, into which is dissolved a water soluble or substantially water soluble active ingredient, i.e., vitamin C or ascorbic acid, which is insoluble or substantially insoluble in an anhydrous base.

The second emulsion phase includes an oil, preferably selected from at least one silicone oil fluid, paraffin oils, vegetable oils, and mixtures thereof.

The invention also provides emulsions for topical administration comprising first and second emulsion phases and a dispersing agent(s). In this aspect, the first emulsion comprises PEG and a water soluble active ingredient which is insoluble or substantially insoluble in an anhydrous base. The second emulsion in this aspect comprises at least one silicone oil fluid.

Testing has shown that the improved topical application emulsions of the invention are suitable for forming stable vitamin C and other topical application products, which may be formulated with or without up to approximately 10% water, and which prove to have an acceptable stability.

The improved topical application emulsions of the present invention may be preferably applied to the skin of an individual in a gelatin capsule, which surrounds and encloses the emulsion, and which may be packaged therein according to known encapsulation methods. Particularly preferred gelatin capsules for use in the invention are "twist-off" gelatin capsules.

The invention further encompasses compositions and methods for treating and/or preventing skin damage caused by exposure to ultraviolet-A (UV-A) and ultraviolet-B (UV-B) radiation, including solar radiation. The inventive compositions include vitamin C dissolved or suspended in the topical emulsions of the invention. Further, such compositions are preferably administered to an individual or patient by way of a soft gelatin "twist-off" capsule. A gelatin capsule is a particularly preferred means for administering the vitamin C topical emulsion since the gelatin capsule prevents or decreases the oxidation of vitamin C by oxygen in the environment. Thus, the invention provides methods for antioxidant skin therapy, and specifically methods for treating or preventing UV-B radiation-induced erythema, photoaging of the skin, skin cancer, etc.

Further details and the substantial advantages of the improved topical application emulsions of the present invention will become more readily apparent to those skilled in the art upon review of the following detailed description of preferred embodiment, brief description of the drawing, the examples thereof and the appended claims.

DETAILED DESCRIPTION OF PREFERRED EMBODIMENTS

Figure 1:
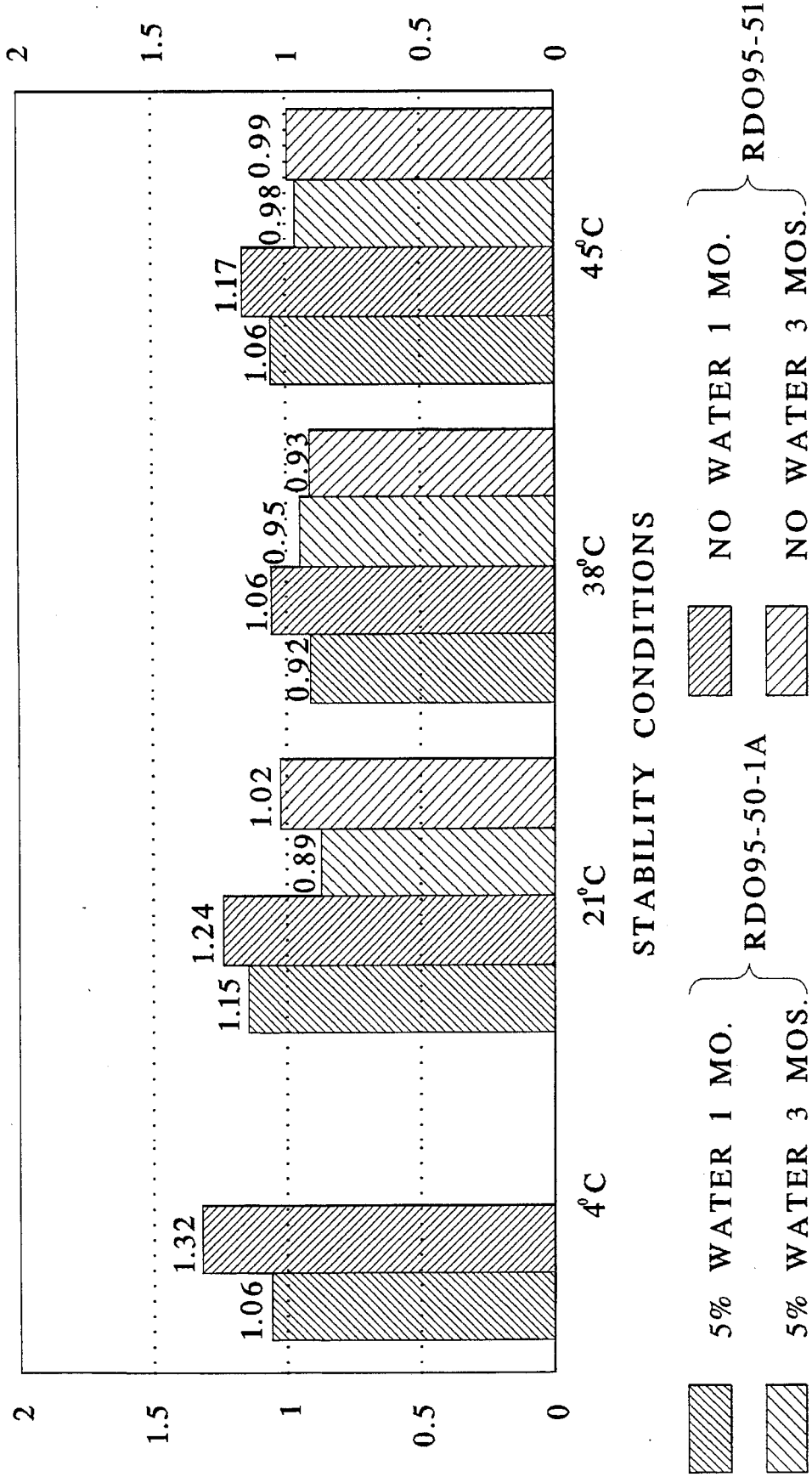
FIG. 1 is a graph showing stability of vitamin C in vitamin C containing emulsions after 3 months at various temperatures, and comparing formulations made with no water versus 5% water.

The improved emulsions for topical application of the present invention are especially adapted for carrying at least one desired water soluble active ingredient that is insoluble or substantially insoluble in an anhydrous base.

Preferred embodiments of the emulsions of the present invention for topical application include first and second emulsion phases, along with a dispersing agent(s) to create an emulsion therebetween, utilizing procedures which are described in greater detail in the Examples set forth below.

In a particularly preferred embodiment, the first emulsion phase hereof includes polyethylene glycol as a solvent, and ascorbic acid (vitamin C) which is insoluble or substantially insoluble in an anhydrous base, and which may be preferably dissolved into the polyethylene glycol solvent.

The second emulsion phase comprises an oil or mixtures of oils. Suitable oils include silicone-derivative silicone oil fluids, paraffin oils, vegetable oils and mixtures thereof. A preferred second emulsion phase comprises at least one silicone-derivative silicone oil fluid, and an oil selected from the group consisting of paraffin oils, vegetable oils and mixtures thereof, some selected examples of which are set forth hereinafter.

In another preferred embodiment, the first emulsion phase includes polyethylene glycol, a water soluble active ingredient which is insoluble or substantially insoluble in an anhydrous base, and which may be preferably dissolved into the polyethylene glycol. In this embodiment, the second emulsion phase comprises a silicone-derivative silicone oil fluid.

The first emulsion phases of the invention may be solutions, suspensions, or dispersions of the active ingredient in the polyethylene glycol. Thus, the active ingredient may be substantially insoluble in the polyethylene glycol phase, i.e., the first emulsion phase.

As used herein, the term "gelatin compatibility" means no adverse interaction of the fill material with the gelatin capsule.

Actual testing by the inventors of the present invention has shown that the applicants' improved topical application emulsions are suitable for forming stable vitamin C topical application products, which may be formulated with or without up to approximately 10% water, and which prove to have an acceptable stability. Other active ingredients have similarly been formulated into stable and useful emulsions according to the principles and teaching of the present invention.

By "stable vitamin C topical emulsion application product" and "stable topical application emulsion" are meant topical application emulsions that do not exhibit creaming, sedimentation, or phase separation.

It has been discovered that there is surprisingly little decomposition of vitamin C in the inventive topical application emulsions.

In one preferred embodiment, for example, the quantity of vitamin C which may be formulated for use in the improved emulsions of the present invention may comprise from about 0.1 to 10, more preferably from about 1.5 to 5, and most preferably about 1.5, weight percent of the total emulsion.

In some preferred embodiments, the first emulsion phase of the improved topical application emulsions invention may further include glycerin, and may also include water up to approximately 10 weight percent by total. However, water, and especially at elevated temperature levels, adversely effects the integrity of gelatin capsules since gelatin is water soluble. Accordingly, when the topical application emulsions are intended for encapsulation in gelatin capsules, the use of substantial amounts of water in the emulsions of the present invention must be closely monitored. The first emulsion phase may also include sodium chloride, and other ingredients, as described in the Examples hereof.

The second emulsion phase may, in addition to including at least one silicone-derivative silicone oil fluid, also contain a paraffin oil such as, for example, mineral oil and/or a vegetable oil.

The polyethylene glycol of the first phase of the improved topical application emulsions of the present invention may be included in amounts of approximately 20–80, and preferably 20–50, weight percent in preferred embodiments.

Suitable polyethylene glycols for use in the topical application emulsions have molecular weights of from about 200 to 6000, and preferably from 400 to 1000.

In addition to vitamin C, other representative water soluble active ingredients include, for example, glycolic acid, MFA fruit complex, other active ingredients, and mixtures thereof, in amounts of up to about 20 weight percent.

One dispersing agent suitable for use in the improved topical application emulsions of the present invention is a polysorbate. Representative polysorbates include Tween 20, a product of ICI Corporation described as a Polysorbate 20, and Tween 80, described as a Polysorbate 80.

The silicone-derivative silicone oil of the second phase of the present invention may comprise approximately 0–50, and preferably 0–40, weight percent of the final topical emulsion. As used herein the term "silicone derivative silicone oil" refers to one or more ingredients of the kind generally known to those skilled in the art as "silicon oil." Examples without limitation include:

| | |
|---|---|
| Silicone Fluids 244, 245, 344, 345 | Cyclomethicone |
| Silicone Fluid Q2-5200 | Laurylmethicone Copolyol |
| Silicone Fluid 3225C | Cyclomethicone and Dimethicone Copolyol |
| Abil WE09 | Polyglyceryl-4 Isostearate and Cetyl Dimethicone Copolyol and Hexyl Laurate |
| Dow Corning 200 (various viscosities) | Dimethicone |

-continued

| | |
|---|---|
| Dow Corning 1401 Fluid | Cyclomethicone and Dimethiconol |
| Dow Corning 1403 Fluid | Dimethicone and Dimethiconol |

The improved topical application emulsions of the present invention are set forth in the following Examples.

Preparation of Emulsions

The emulsions are made according to techniques known to those skilled in the art. Preservative and fragrance may optionally be added to the resulting emulsion formulations.

Once the appropriate emulsion is formulated, it can be encapsulated into conventional soft gelatin capsules in accordance with the rotary die process. Alternatively, the emulsions can be appropriately encapsulated in hard shell gelatin capsules as well as soft gelatin capsules.

Unless noted otherwise, the components listed for each of the formulations described in the following examples are indicated in parts by weight.

EXAMPLES 1, 2, AND 3

| | Example 1 (RDO95-51-2) | Example 2 (RDO95-50-1A) | Example 3 |
|---|---|---|---|
| Phase I | | | |
| PEG-400 | 68.25 | 63.24 | 64.75 |
| Vitamin C-Ascorbic Acid | 1.50 | 1.50 | 1.50 |
| Glycerin-USP | 5.00 | 5.00 | 5.00 |
| Water | — | 5.00 | 5.00 |
| Sodium Chloride | — | 0.25 | 0.25 |
| Phase II | | | |
| Silicone Fluid 245 | 15.00 | 15.00 | 15.00 |
| Silicone Fluid 3225C | 9.00 | 9.00 | 9.00 |
| Tween-20 | 1.50 | 1.50 | 1.50 |
| 5-Freeze Thaw Cycles | Acceptable | Acceptable | Acceptable |
| 40° C. Oven Stability | Acceptable | Acceptable | Acceptable |
| Room temperature Stability | Acceptable | Acceptable | Acceptable |
| Gelatin capsule compatibility | Acceptable | Acceptable | Acceptable |

The emulsions of Examples 1, 2 and 3 were made according to blending methods and procedures known to those skilled in the art.

The stability of vitamin C in the Example 1 and Example 2 formulations in terms of the percent by weight of active vitamin C remaining in the formulation after exposure to various temperatures for 90 days is shown in FIG. 1.

EXAMPLES 4 and 5

| | Example 4 | Example 5 |
|---|---|---|
| Phase I | | |
| PEG-400 | 58.75 | 36.00 |
| Vitamin C-Ascorbic Acid | 1.50 | 1.50 |
| Glycerin-USP | — | 5.00 |
| Ethoxylated-26 Glycerin | — | 13.25 |
| Water | 8.00 | 8.80 |
| Sodium Chloride | 0.25 | 0.25 |
| Pfaffia extract | — | 0.28 |
| Pycnogenol | — | 0.14 |
| Ecchnesia Extract | — | 0.28 |
| Phase II | | |
| Mineral oil | — | 25.00 |
| Dow Corning Fluid 244 | 15.00 | 2.00 |
| ABIL WE 09 | — | 5.00 |
| Tween-20 | 2.50 | — |
| Dow Corning Fluid 3225C | 9.00 | — |
| Borage Oil | — | 1.00 |
| Vit-E Linoleate | — | 0.50 |
| Vit-A Palmitate | — | 0.50 |
| Crodoram Rhatania "O" | — | 0.33 |
| Crodoram Nut "O" | — | 0.16 |
| Caroplex | — | 0.01 |
| 5-Freeze Thaw Cycles | Acceptable | Acceptable |
| 40° C. oven Stability | Acceptable | Acceptable |
| Room temperature stability | Acceptable | Acceptable |
| Gelatin capsule compatibility | Acceptable | Acceptable |

Stable PEG/Silicone Cream Formulations

| Ingredient | Example 6 (RDO91-118-2) |
|---|---|
| Phase 1: | |
| Transcutol | 18.95 |
| PEG-1000 | 15.10 |
| PEG-400 | 15.20 |
| Glycerin-USP | 5.00 |
| Water | 2.00 |
| Glycolic Acid | 1.00 |
| MFA Fruit Acid | 3.00 |
| Germal 115 | 0.30 |
| Phase 2: | |
| Synchrowax HR-C | 3.00 |
| D/C Silicone 345 | 20.55 |
| D/C Silicone 3225C | 11.50 |
| D/C Silicone 556 | 2.00 |
| Tween-20 | 2.00 |
| Liquipar Oil | 0.10 |
| Fragrance F94-238 | 0.30 |
| 5-Freeze Thaw Cycles | Acceptable |
| 40° C. Oven Stability | Acceptable |
| Room temperature stability | Acceptable |
| Gelatin capsule compatibility | Acceptable |

Mineral Oil/PEG Emulsions

| Ingredient | Example 7 (RDO95-31-1) | Example 8 (RDO95-40) |
|---|---|---|
| Phase I: | | |
| PEG-400 | 53.55 | 36.00 |
| Ethoxylated-7 Glycerin | — | 13.25 |
| Glycerin-USP | 5.00 | 5.00 |
| Water | 7.70 | 8.00 |
| Sodium Chloride | 0.25 | 0.25 |
| Vitamin-C (Ascorbic Acid) | 1.50 | 1.50 |
| Pfaffia/Ecchenesia/ | — | 1.25 |

Mineral Oil/PEG Emulsions

| Ingredient | Example 7 (RDO95-31-1) | Example 8 (RDO95-40) |
| --- | --- | --- |
| Pycnogenol | | |
| Phase II: | | |
| Mineral Oil | 25.00 | 25.00 |
| D/C Fluid 244 | 2.00 | 2.00 |
| Abil WE09 | 5.00 | 5.00 |
| Borage Oil | — | 1.00 |
| Vit-E Linoleate | — | 0.50 |
| Vit-A Palmitate | — | 0.50 |
| Rhatania extract | — | 0.50 |
| Crodoram Nut "O" | — | 0.25 |
| 5-Freeze Thaw Cycles | Acceptable | Acceptable |
| 40° C. Oven Stability | Acceptable | Acceptable |
| Room temperature Stability | Acceptable | Acceptable |
| Gelatin capsule compatibility | Acceptable | Acceptable |

Vegetable Oil/Silicone Emulsions

| Ingredient | Example 9 (RDO95-39-1) | Example 10 (RDO95-39-2) |
| --- | --- | --- |
| Phase I: | | |
| PEG-400 | 53.55 | 36.00 |
| Ethoxylated-7 Glycerin | — | 13.25 |
| Vitamin-C (Ascorbic Acid) | 1.50 | 1.50 |
| Glycerin | 5.00 | 5.00 |
| Water | 7.70 | 8.00 |
| Sodium Chloride | 0.25 | 0.25 |
| Phase II: | | |
| Olive Oil | 25.00 | 25.00 |
| Silicone Fluid 244 | 2.00 | 2.00 |
| Abil WE09 | 5.00 | 5.00 |
| Borage Oil | — | 2.00 |
| 5-Freeze Thaw Cycles | Acceptable | Acceptable |
| 40° C. Oven Stability | Acceptable | Acceptable |
| Room temperature Stability | Acceptable | Acceptable |
| Gelatin capsule compatibility | Acceptable | Acceptable |

The following table lists the source and generic name of various materials employed or suitable for use in the compositions of the invention.

| Ingredient | Source | Generic Name |
| --- | --- | --- |
| PEG-400, PEG-600, PEG-1000 | Union Carbide | Polyethylene Glycol |
| Silicone Fluids 244, 245, 344, 345 | Dow-Corning | Cyclomethicone |
| Silicone Fluid 3225C | Dow-Corning | Cyclomethicone and Dimethicone Copolyol |
| Tween-20 | ICI Americas | Polysorbate-20 |
| Protochem GL-7, GL-26 | Protameen Chemical | Ethoxylated-7 Glycerin and Ethoxylated-26 Glycerin |
| ABIL WE-09 | Goldschemidt | Polyglyceryl-4 Isostearate and cetyl Dimethicone Copolyol and Hexyl Laurate |
| Down-Corning Fluid 200 | Dow-Corning | Dimethicone |
| Dow-Corning Fluid 1401 | Dow-Corning | Cyclomethicone and Dimethiconol |
| Dow-Corning Fluid 1403 | Dow-Corning | Dimethicone and Dimethiconol |
| Ceraphyl 31 | ISP-Vandyk | Lauryl Lactate |
| Scheremol DIA | Scher and Co. | Diisopropyl Adipate |
| MFA-Complex | Barnett and Co. | Alpha hydroxy Acid Complex |
| Dry-Flow PC | National Starch | Aluminum Starch Octylsuccinate |
| Syncrowax HR-C | Croda | Glyceryl Behenate |
| Crodoram Rhatania "O" | Croda | Rhatania Root Extract |
| Crodoram Nut "O" | " | Walnut Extract |
| Caroplex | Quest | Caroteen Mixture |
| Pfaffia | NAT-TROP | Pfaffia extract |
| Echenesia extract | East Earth herb | Coneflower extract |
| Pycnogenol | TAAG and Co. | Maritme Pine extract |
| Borage Oil | Cannamino and Co. | Borage Oil |
| Vitamin E Linoleate | Hoffman-LaRoche | Tocopheryl linoleate |
| Vitamin A Palmitate | Hoffman-LaRoche | Retinyl palmitate |

The basic and novel characteristics of the improved methods, compositions of matter, and combination of ingredients of the present invention will be readily understood from the foregoing disclosure by those skilled in the art. It will become readily apparent that various changes and modifications may be made in the form, construction and arrangement of the improved formulations of the present invention, and in the steps of the inventive methods hereof, which various respective inventions are as set forth hereinabove without departing from the spirit and scope of such inventions. Accordingly, the preferred and alternative embodiments of the present invention set forth hereinabove are not intended to limit such spirit and scope in any way.

What is claimed is:

1. A soft gelatin capsule comprising a shell and an emulsion for carrying vitamin C comprising:

first and second emulsion phases, and a dispersing agent;

said first emulsion phase including, as a solvent, polyethylene glycol, and vitamin C dissolved into said polyethylene glycol solvent; and said second emulsion phase comprising a silicone-derivative silicone oil fluid.

2. The gelatin capsule of claim 1 wherein said vitamin C initially comprises approximately 0.1 to 10 weight percent of the total emulsion.

3. The gelatin capsule of claim 1 wherein said first emulsion phase further comprises glycerin.

4. The gelatin capsule of claim 1 wherein said first emulsion phase further comprises up to about 10% water based on the weight of the emulsion.

5. The gelatin capsule of claim 1 wherein said second emulsion phase further comprises mineral oil.

6. The gelatin capsule of claim 1 wherein said second emulsion phase further comprises a vegetable oil.

7. A soft gelatin capsule comprising:

a gelatin shell; and a fill material provided within the shell,
the fill material being an emulsion comprising from about 0.1 to 10% by weight of ascorbic acid based on the weight of the fill material, polyethylene glycol as a solvent, and a silicone oil.

8. A gelatin capsule according to claim 7, further comprising from about 0.5 to 10% of water in the fill material, based on the weight of the fill material.

* * * * *